(12) United States Patent
Zavaleta (10) Patent No.: US 10,288,568 B2
(45) Date of Patent: May 14, 2019

(54) RAMAN PROBE AND METHODS OF IMAGING

(71) Applicant: The Board of Trustees of the Leland Stanford Junior University, Palo Alto, CA (US)

(72) Inventor: Cristina Zavaleta, Los Angeles, CA (US)

(*) Notice: Subject to any disclaimer, the term of this patent is extended or adjusted under 35 U.S.C. 154(b) by 0 days.

(21) Appl. No.: 15/835,608

(22) Filed: Dec. 8, 2017

(65) Prior Publication Data
US 2018/0164218 A1 Jun. 14, 2018

Related U.S. Application Data

(60) Provisional application No. 62/431,520, filed on Dec. 8, 2016.

(51) Int. Cl.
| | |
|---|---|
| *G01J 3/44* | (2006.01) |
| *G01N 21/65* | (2006.01) |
| *G01J 3/02* | (2006.01) |
| *A61B 5/00* | (2006.01) |
| *A61B 1/07* | (2006.01) |
| *G01N 21/64* | (2006.01) |
| *B82Y 15/00* | (2011.01) |

(52) U.S. Cl.
CPC .......... *G01N 21/658* (2013.01); *A61B 1/07* (2013.01); *A61B 5/00* (2013.01); *A61B 5/0075* (2013.01); *A61B 5/0084* (2013.01); *G01J 3/02* (2013.01); *G01J 3/0221* (2013.01); *G01J 3/44* (2013.01); *G01J 3/4406* (2013.01); *G01J 3/4412* (2013.01); *G01N 21/6456* (2013.01); *G01N 21/65* (2013.01); *B82Y 15/00* (2013.01); *G01N 2021/6439* (2013.01)

(58) Field of Classification Search
CPC ........ G01N 21/78; G01N 21/76; G01N 21/64; G01N 21/65; G01N 35/10; H01L 31/167; F21V 8/00; G01J 3/46; G01J 3/02
See application file for complete search history.

(56) References Cited

U.S. PATENT DOCUMENTS

| | | | |
|---|---|---|---|
| 2011/0108707 A1* | 5/2011 | Cui | A61B 5/0059 250/208.1 |
| 2013/0010340 A1* | 1/2013 | Birk | G02B 21/002 359/200.7 |
| 2014/0226157 A1* | 8/2014 | Dogariu | G01J 3/44 356/301 |

* cited by examiner

*Primary Examiner* — Abdullahi Nur
(74) *Attorney, Agent, or Firm* — Thomas|Horstemeyer, LLP; Stephanie Davy-Jow; Christopher Linder

(57) ABSTRACT

The present disclosure provides for a Raman probes and methods of imaging including a Raman probe. The Raman probes include a Raman detection system configured to illuminate an area of a subject or a sample with a light source and to receive Raman scattered light energy from the area. The Raman probe can include a proximity sensor system and a fluorescent imaging system. A method of imaging introduces a Raman probe to a subject. Fluorescent light is detected from an area of the subject, which guides the Raman probe to the area. The Raman probe is positioned at a target distance from the area using the proximity sensor system, and by exposing the area to a light beam from the Raman detection system. The light beam, Raman scattered light energy, is scattered by a Raman agent associated with the area. Raman scattered light is detected using the Raman imaging device.

5 Claims, 4 Drawing Sheets

RAMAN PROBE AND METHODS OF IMAGING

CROSS-REFERENCE TO RELATED APPLICATIONS

This application claims the benefit of and priority to U.S. Provisional Application Ser. No. 62/431,520, having the title "RAMAN PROBE AND METHODS OF IMAGING", filed on Dec. 8, 2016, the disclosure of which is incorporated herein by reference in its entirety.

STATEMENT REGARDING FEDERALLY SPONSORED RESEARCH OR DEVELOPMENT

This invention was made with Government support under contracts CA160834 and CA184608 awarded by the National Institutes of Health. The Government has certain rights in the invention.

BACKGROUND

One of the biggest challenges that surgical oncologists face in the operating room (OR) is determining where the tumor they are resecting begins and ends. Obtaining negative tumor margins can be essential to the patient's survival. However, the tools available to surgeons during the actual resection are limited to non-existent. As a result, positive tumor margins are often left which can lead to another expensive trip to the OR for re-excision along with more imaging and pathology costs.

SUMMARY

The present disclosure provides for a Raman probe including a Raman detection system, wherein the Raman detection system is configured to illuminate an area of a subject or a sample with a light source and to receive Raman scattered light energy from the area. The Raman probe also includes a proximity sensor system configured to measure the distance from the Raman probe to the area; and, optionally a fluorescent imaging system configured to detect fluorescence from the area. A method of imaging is also described, which includes introducing a Raman probe to a subject. The method can also include detecting, optionally, fluorescent light from an area of the subject and guiding, optionally, the Raman probe to the area based on the detected fluorescent light. The method can also include positioning the Raman probe at a target distance from the area, wherein the positioning at the target distance is determined using the proximity sensor system, and exposing the area to a light beam from the Raman detection system. The light beam is scattered by a Raman agent associated with the area. The light beam that is scattered is referred to as a Raman scattered light energy. The method can also include detecting the Raman scattered light using the Raman imaging device.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure.

FIGS. 2A-B are example embodiments of the optics architecture (FIG. 2A), including the wide-field fluorescent imager and the Raman spectrometer.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biochemistry, biology, molecular biology, imaging, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

The term "administration" refers to introducing an agent (or a compound, cell, or virus, including the agent, where the agent can be a Raman agent or fluorescent agent, for example) of the present disclosure into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used. In an embodiment, the agent is administered locally (e.g., colon) so that it is not systemically distributed throughout the body.

In accordance with the present disclosure, "a detectably effective amount" of the agent (e.g., a Raman agent such as a SERS nanoparticle) of the present disclosure is defined as an amount sufficient to yield an acceptable image using equipment that is available for pre-clinical or clinical use. In an embodiment, a detectably effective amount of the agent of the present disclosure may be administered in more than one injection. The detectably effective amount of the agent of the present disclosure can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and digital processing related factors. Optimization of such factors is well within the level of skill in the art.

As used herein, the term "subject" includes humans, mammals, and birds (e.g., mice, rats, pigs, cats, dogs, birds, and horses,). Typical subjects to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to host or organisms noted above that are alive. The term "living subject" refers to the entire host or organism and not just a part excised (e.g., a liver or other organ) from the living subject.

As used herein, the term "in vivo imaging" refers to imaging living subjects (e.g., human or mammals).

The term "Surface-Enhanced Raman Scattering (SERS)" refers to the increase in Raman scattering exhibited by certain molecules in proximity to certain metal surfaces. (see, U.S. Pat. No. 5,567,628) The SERS effect can be enhanced through combination with the resonance Raman effect. The surface-enhanced Raman scattering effect is even more intense if the frequency of the excitation light is in resonance with a major absorption band of the molecule being illuminated. In short, a significant increase in the intensity of Raman light scattering can be observed when molecules are brought into close proximity to (but not necessarily in contact with) certain metal surfaces. In an embodiment, the metal surfaces can be "roughened" or coated with minute metal particles. Metal colloids also show this signal enhancement effect. The increase in intensity can be on the order of several million-fold or more.

The term "reporter compound" can refer to a Raman-active label. The term "Raman-active label" can refer to a substance that produces a detectable Raman spectrum, which is distinguishable from the Raman spectra of other components present, when illuminated with a radiation of the proper wavelength.

As used herein, the term "Raman agent" refers to the compounds or structures of the present disclosure that are capable of serving as imaging agents either alone or in combination with attached molecules (e.g., antibodies, proteins, peptides, small organic molecules, aptamers, and the like).

Discussion

In accordance with the purpose(s) of the present disclosure, as embodied and broadly described herein, embodiments of the present disclosure, in one aspect, relate to Raman probes or systems, methods of using the Raman probe, and the like. Embodiments of the present disclosure seek to improve detection of a disease or condition using a Raman probe, where the Raman probe could be used in conventional intraoperative, endoscopic, laparoscopic, or surgical procedures.

In an embodiment, the Raman probe can be used in conjunction with one or more types of Raman agents, where each produce a detectably distinguishable Raman light scattering signal, where the Raman detection system can excite each of the Raman agents with light and sensitively detect Raman scattered light energy signals emitted from each of the Raman agents. In particular, the Raman probe can be used in conjunction with Raman agents that target a specific disease to detect it earlier and at its margins with greater sensitivity than what is currently used.

In addition, embodiments of the present disclosure can be advantageous in that an embodiment of the Raman probe can use a proximity sensing system to normalize the Raman signal to reduce the quadratic drop off associated with distance from sample surface. In addition, embodiments of the present disclosure can be advantageous because it can provide a dual modal fluorescence/Raman detection capability. Another embodiment can include the dual modal fluorescence/Raman detection capability and the proximity sensing system.

As a result, embodiments of the present disclosure include methods of using a Raman probe to image, detect, study, monitor, evaluate, and/or screen a subject or resected samples. For example the Raman probe can be used to study the bronchioles, esophagus, colon, rectum, skin, oral mucosa, intraoperatively any organ, and the like, or resected samples therefrom. In an embodiment, the Raman probe can act as an in-vivo histopathological tool assisting the physician to immediately identify a diseased area and its margins without having to involve a third party pathologist.

In an embodiment, the Raman probe includes a Raman detection system and one or both of a fluorescent imaging system and a proximity sensor system. In an embodiment, the Raman detection system can be configured to illuminate an area of interest in a subject or sample with a light source and to receive Raman scattered light energy from the area of interest of the subject or sample, where the light energy is scattered by one or more Raman agents associated with a disease or condition. Additional details are described herein.

In an embodiment, the fluorescent imaging system is configured to detect fluorescence from the area of interest of the subject or sample. In an embodiment, the fluorescent imaging system can include a wide-field fluorescent imager, which can be used to consider a large field of view that can be used to guide the user (e.g., a surgeon) to the area of interest. In an embodiment, the fluorescent imaging system can include the use of an excitation laser, a gradient index (GRIN) optics lens and a camera for wide field emitted light detection.

In an embodiment, a fluorescent agent can be used that can be conjugated with a targeting agent having an affinity for the target area (e.g., tissue, cell, tumor, cancerous tissue, and the like). Additional details regarding fluorescent agents are provided herein.

In an embodiment, the proximity sensor system is configured to measure the distance from the Raman probe to the area of interest. The distance from the Raman probe to the area of interest can play a role of the detection of the Raman scattered light energy. In addition, use of a uniform distance for measuring the Raman scattered light energy from different points on the sample should be done to generate a meaningful topological map of the total of the areas of interest such as a region of tissue in a subject or the surfaces of a sample from a subject. In particular, since there is a $1/r^2$ drop off of the Raman scattered light energy with working distance away from the tissue, use of the proximity sensor system (e.g., time of flight sensor (ST FlightSense™ technology) provides the ability to normalize acquired signals from multiple areas of interest of the tissue. In contrast, if the signals are acquired from different distances, the relative intensity of the signals can obscure the true nature of the tissue. In other words, use of signals acquired from different distance can generate more false positives or false negatives. Thus, use of the proximity sensor system can be used to measure the distance away from the tissue and renormalize the signal due to the quadratic response seen with varying working distances. As a result, the Raman probe including the proximity sensor system can be used to determine differences in spectral Raman intensity in real time and/or to generate a realistic topological map of the tissue or the area of tissue being investigated or of interest.

In an embodiment, the proximity sensor system can include, but is not limited to, sensors found at ST microelectronics. In an embodiment, the proximity sensor can include SparkFun "TimeofFlight" Range Finder®, a sensor board for the VL6180 distance sensor. Unlike most distance sensors that rely on reflected light intensity or reflected angles to determine range, the VL6180 uses a precise clock to measure the time it takes light to bounce back from a surface. As a result, the ToF Range Finder® and VL6180 can provide a more accurate measurement and is influenced by noise to a lower degree.

The target distance can be the distance that one would like to position the probe from the surface of the area (e.g., tissue) to reduce the $1/r^2$ drop off and maximize the Raman signal. In an embodiment, the target distance can be about 0.001 to 50 mm or about 0.001 to 20 mm. In an embodiment, the target distance used for different areas should be about (e.g., ±1 to 10% or 5 to 10%) the same as each other or equal to each other.

Now having described the Raman probe in general, additional detail will be provided. The Raman probe includes one or more channels down the length of the Raman probe. The components of the Raman detection system and one or both of a fluorescent imaging system and the proximity sensor system are positioned within one or more of the channels. In an embodiment, the Raman probe includes a single channel including all of the components. In an embodiment, the outside diameter of the Raman probe can be about 1 to 25 mm or about 20 mm. In an embodiment, the inside diameter of the Raman probe can be about 5 to 15 mm or about 10 mm. In an embodiment, the Raman probe can have a length of about 5 to 20 cm (not including the extended fiber bundle to be attached to the corresponding lasers and spectrometer). Additional details regarding the dimensions and configuration of the Raman probe are provided in the Examples and figures.

In an embodiment the light source is selected from one or more from the following group: a light emitting diode (LED), a laser, a diode laser, and a super luminescent laser diode (SLD). In an embodiment, the Raman probe includes a light source (e.g., a laser) or is adapted to direct a light source (e.g., uses a fiber to guide the light) that may be generated separately from the Raman probe, and a device or structure to receive or detect Raman scattered light energy (e.g., uses a fiber to collect light). In an embodiment, the Raman scattered light energy can then be measured by a device (e.g., a spectrometer/CCD).

Embodiments of the Raman probe can include a fiber bundle, one or more lenses for collimating a light beam (e.g., a laser at a wavelength that the Raman agents scatter the light) and for focusing the fluorescent light and/or Raman scattered light energy, and optionally filters for delivering and collecting the appropriate light signals. Other components can be part of the Raman probe or used in conjunction with the Raman probe (e.g., a Raman probe system) and these include a spectrometer and charge-coupled device (CCD) camera for collection and measurement of inelastically scattered light.

In an embodiment, the Raman detection system can include an optical fiber system to direct light derived from the light source to the area. In addition, the Raman detection system can be used to collect and direct the Raman scattered light energy to the Raman detection system.

In an embodiment, the Raman detection system includes an optic system (e.g., mirrors, lenses, and the like). In an embodiment, an optic system can be disposed between the optical fiber system and the sample to concentrate the light onto the sample. In addition, the optic system can be used to collect the Raman scattered light energy from the sample. In an embodiment, the optic system can capture and concentrate the collected Raman scattered light energy into the optical fiber system.

In an embodiment, the optical fiber system can include a single fiber to guide light derived from the light source to the area. In an embodiment, the optical fiber system can include a fiber bundle to guide Raman scattered light energy from the area to a Raman detection system. In an embodiment, a single mode fiber can be used to direct the light out of the Raman probe while one or more (e.g., 37 fibers) can be used to receive the light (e.g., scattered Raman light energy, fluorescence).

Optionally the Raman probe can include collection and measurement devices or instruments to collect and measure the scattered Raman light energy. In an embodiment the Raman probe can include one or more lenses to guide the light and the scattered Raman light energy, one or more mirrors to direct the laser light or scattered Raman light energy, and/or one or more filters to select certain wavelengths of light and/or scattered Raman light energy.

In an embodiment, a collimating lens can be used. In an embodiment, the collimating lens placement allows for a consistent Raman signal to be produced over a variety of working distances. In an embodiment, the Raman probe can have an illumination range of about 300 nm to 10 mm for light produced for Raman detection. In an embodiment, the Raman/Fluorescent probe can have an illumination range of about 300 nm to 10 mm for fluorescent detection.

In an embodiment, enabling software can display (in order to inform the user/physician) the relative signal strength of received signal (e.g., fluorescent and/or Raman signal) as well as the ratio signal strength (e.g., for embodiments including different types Raman agents).

In an embodiment, an ultrasound transducer array can be incorporated into the Raman probe. With an array of ultrasound transducers, photoacoustic or ultrasound imaging can be performed.

An embodiment of the present disclosure includes a method of imaging an area or multiple areas of a tissue in a subject or a resected tissue from a subject. In an embodiment, the method includes introducing a Raman probe as described herein to a subject. In an embodiment, the Raman probe can be introduced to the subject (e.g., human) who is undergoing a procedure (e.g., surgical, laparoscopic, intraoperative, or endoscopic procedure), where the Raman probe or a device including the Raman probe is inserted into the body (e.g., cervix, bladder, bronchioles, esophagus, stomach, colon, rectum, skin, oral mucosa, and intraoperatively or laparoscopically into an organ, and the like) or placed over the region of interest (during surgical or intraoperative procedures).

Subsequently, the Raman probe can be used to detect a fluorescent light from a first area of the subject or sample. The Raman probe can be used to cause the production of the fluorescent light signal from the area. As mentioned herein, the Raman probe can direct a light onto the area and a fluorescent signal can be produced from a fluorescent agent associated with the area (e.g., a target fluorescent agent having an affinity for a target (e.g., cancerous cells or tissue, tumor)) or generated by the native tissue. The received fluorescent signal can be used to guide the Raman probe to the first area of interest based on the detected fluorescent light, where the detected fluorescent light is associated with the target. In other words, the fluorescent signal can be used as a broad guide to the area of interest, and a more refined and detailed image can be accessed using scattered Raman light energy as discussed below.

Once the area of interest is determined, the Raman probe can be positioned at a target distance from the area of interest. The positioning at the target distance is determined using the proximity sensor system. As discussed herein, the target distance is used to maximize the detected scattered Raman light energy and/or normalize the distance from the area of interest.

Once positioned, the area of interest can be exposed to a light beam from the Raman detection system. The light can be scattered by a Raman agent associated with the area of interest, where the light that is scattered is referred to as a Raman scattered light energy. The Raman probe can be used to detect the Raman scattered light energy.

One of the principles by which embodiments of the present disclosure operates is based on the Raman Effect. When light is scattered from a molecule most photons are elastically scattered. However, a small fraction of light is scattered at optical frequencies different from and usually lower than the frequency of the incident photons. The process leading to this inelastic scatter is termed the Raman Effect. However, this effect can be relatively weak, only producing one inelastically scattered photon for every 10 million elastically scattered photons.

In an embodiment, surface enhanced Raman scattering (SERS) agents can be used. SERS is a plasmonic effect where small molecules adsorbed onto a nano-roughened noble metal surface, for example, experience a dramatic increase in the incident electromagnetic field resulting in several orders of magnitude higher Raman intensity. The increase in the Raman Effect allows embodiments of the present disclosure to detect pM concentrations of Raman agents with the Raman imaging device. The Raman agents can be selected so that they include unique Raman active molecules (that can be interchanged for multiplexing capabilities) adsorbed onto a metal core.

In an embodiment, the fluorescent and/or Raman agents can be conjugated to a disease targeting agent or ligand that has an affinity for and a binding potential to the diseased area as opposed to normal tissue. Once the agent has been conjugated to the appropriate disease targeting ligand or agent, the agent can be administered to the subject and the agent is given an appropriate amount of time to bind to the targeted disease (e.g., diseased tissue or cells or compounds associated with the disease). Subsequently, using the Raman probe, a light beam can be directed onto the area of interest (e.g., which may include the suspected diseased area) to detect fluorescent signal or the inelastic scattered energy (Raman scattering light energy) coming from disease targeted Raman agents (or the tissue).

As mentioned above, embodiments of the present disclosure include using Raman agents to locate and detect a signal from a diseased area of interest. In an embodiment, the Raman agents give a much more intense Raman signal than the intrinsic Raman scattering from the tissues themselves (e.g., about $10^7$ orders of magnitude greater) allowing the achievement of at least pM sensitivity.

As mentioned above, the Raman probe can be used to measure a signal, where the signal originated from a particular location. In an embodiment, the Raman probe, in conjunction with an analysis system (e.g., computer, software, etc., are interfaced with the Raman probe), is capable of creating an image of an examined area of a living host (e.g., colon), which is in contrast to just measuring a signal in a host. In addition, the Raman probe can examine multiple areas of the tissue and generate a topological map of the tissue.

A Raman image (e.g., the Raman scattered light energy) using embodiments of the present disclosure is different from a bulk signal in that the Raman image is a visual representation of signal as a function of location (e.g., a particular location in the host such as a part (e.g., a few millimeters, a centimeter or more) of the colon or the like).

In an embodiment, the same sequence of steps can be performed for a plurality of different areas. In this way a topological map of the tissue of interest can be produced. The area(s) can include a portion or the entire area of the: cervix, bladder, bronchioles, esophagus, stomach, colon, rectum, skin, oral mucosa, and intraoperatively or laparoscopically an organ. In an embodiment, the mapping can be conducted by exposing the area to the Raman probe by moving the Raman probe. An area can be mapped prior to and/or after introducing one or more types of Raman agents and/or one or more types of biological agents to the subject or sample. The Raman probe detects the Raman scattered light and this can be correlated to a position in the area so that a map can be obtained for the area. In an embodiment, the area can be monitored as a function of time and can be used to determine the impact of a particular treatment or the like.

In another embodiment of the present disclosure, the Raman probe can be combined with an anatomical image and/or a functional image of the same subject generated from an anatomical imaging system. The anatomical imaging system can include, but is not limited to, bright field white light imaging, computer topography (CT), ultrasound, magnetic resonance imaging (MRI), and the like. The combination of multiple functional images or a functional image with an anatomical image would provide more useful information about the exact location of a specific molecular event. The anatomy would tell where, and the molecular image (functional image) would tell how much molecular signal from a given anatomical coordinate.

Embodiments of the present disclosure can also be used to identify the surgical margins for a tumor resection. In particular, a surgeon can use the imaging information provided by embodiments of the present disclosure to guide surgery. Embodiments of the present disclosure can be used for in-situ morphological mapping, in particular, to map cancer tissue to guide therapy. Embodiments of the present disclosure can be used to develop an understanding of the morphological composition of a tumor at the molecular level and optimize their therapies accordingly. Embodiments of the present disclosure can also be used for targeted thermal ablation. The therapy could take advantage of the energy-absorbing properties and the targeting properties of the nanoparticles to thermally ablate tumor cells.

Raman Agents and Fluorescent Agents

The Raman agents can include Raman compounds and Raman nanoparticles. In an embodiment, the Raman compounds can include reporter compounds conjugated with one or more distinct targeting agents, both of which are described in more detail below. In an embodiment, the Raman nanoparticles include, but are not limited to, SERS nanoparticles, composite organic inorganic nanoparticles (COINS), Single walled nanotubes (SWNTs), methylene blue dye (other Raman active dyes), and the like. Each of the Raman nanoparticles can include targeting ligands (e.g., proteins) so that targeted areas (e.g., organs (e.g., colon or breast), and the like) can be imaged.

In an embodiment, the SERS nanoparticle includes, but is not limited to, a core, a reporter compound, and an encapsulant material. The encapsulant material covers and protects the core and reporter compounds. The reporter compounds are attached to the core. The core can be made of materials such as, but not limited to, copper, silver, gold, and combinations thereof, as well as of other metals or metalloids. Different types of SERS nanoparticles can be selected, where each SERS nanoparticle has a different Raman signature. Thus, the use of different SERS nanoparticles enables multiplexing. Additional details regarding this particular type of SERS nanoparticle is provided in WO 2006/073439, U.S. Pat. No. 6,514,767, and U.S. Patent Application No. 60/557,729, each of which are incorporated herein by reference as they pertain to the detailed description of each application or patent and as they relate to SERS nanoparticles and SACNs.

In an embodiment, one type of SERS nanoparticle includes Surface Enhanced Spectroscopy-Active Composite Nanoparticles (SACNs). SACNs and methods of making SACNs are described in WO 2006/073439, U.S. Pat. No. 6,514,767, and U.S. Patent Application No. 60/557,729, each of which is incorporated herein by reference as they pertain to the detailed description of each application or patent and as they relate to SACNs. Embodiments of the SACNs can include a SERS nanoparticle, a submonolayer, monolayer, or multilayer of reporter molecules in close proximity to the metal surface, and an encapsulating shell (e.g., a polymer, glass ($SiO_x$), or other dielectric material). In an embodiment, the reporter compound is disposed at the interface between the SERS nanoparticle and the encapsulant. In an embodiment, a SACN comprises (i) a metal nanoparticle core (e.g., Au or Ag), (ii) a Raman-active reporter (reporter compound), that gives a unique vibrational signature, and (iii) an $SiO_x$:encapsulant that "locks" the reporter molecules in place while also providing a highly compatible surface for subsequent immobilization of biomolecules. The glass coating can also stabilize the particles against aggregation and can prevent competitive adsorption of unwanted species. In an embodiment, the SERS nanoparticles are comprised of polymer coatings adjacent to the nanoparticle.

As used herein, the term "reporter compound" includes Raman-active compounds that produce a unique SERS signature in response to excitation by a laser. In certain embodiments, Raman-active organic compounds are polycyclic aromatic or heteroaromatic compounds. In an embodiment, the reporter compound can include, but is not limited to, 4-mercaptopyridine (4-MP); trans-4,4'bis (pyridyl)ethylene (BPE); quinolinethiol; 4,4'-dipyridyl, 1,4-phenyldiisocyanide; mercaptobenzamidazole; 4-cyanopyridine; 1',3,3,3',3'-hexamethylindotricarbocyanine iodide; 3,3'-diethyltiatricarbocyanine; malachite green isothiocyanate; bis-(pyridyl)acetylenes; Bodipy; TRIT (tetramethyl rhodamine isothiol); NBD (7-nitrobenz-2-oxa-1,3-diazole); Texas Red dye; phthalic acid; terephthalic acid; isophthalic acid; cresyl fast violet; cresyl blue violet; brilliant cresyl blue; para-aminobenzoic acid; erythrosine; biotin; digoxigenin; 5-carboxy-4',5'-dichloro-2',7'-dimethoxy fluorescein; 5-carboxy-2',4',5',7'-tetrachlorofluorescein; 5-carboxyfluorescein; 5-carboxy rhodamine; 6-carboxyrhodamine; 6-carboxyletramethyl amino phthalocyanines; azomethines; cyanines; xanthines; succinylfluoresceins; aminoacridine; fullerenes; organocyanides (e.g., isocyanide), methylene blue indigo carmine, and indocyanine green (ICG), and the like, and combinations thereof.

A COIN includes several fused or aggregated primary metal crystal particles with the Raman-active organic compounds (reporter compound) adsorbed on the surface, within the junctions of the primary particles, or embedded in the crystal lattice of the primary metal particles. The primary metal crystal particles are about 15 nm to 30 nm, while the fused or aggregated COIN is about 50 nm to about 200 nm. The primary metal crystal particle is made of materials such as, but not limited to, gold, silver, platinum copper aluminum, and the like. The Raman-active organic compound refers to an organic molecule that produces a unique SERS signature in response to excitation by a laser. Additional details regarding COINS are described in U.S. Patent Applications 20050142567, 20060234248, and 20070048746, each of which is incorporated herein by reference for the corresponding discussion.

COINs can also serve as Raman nanoparticles to provide imaging signals. The COINs can be functionalized so they have better solubility in blood and can target potential targets in a living subject. Multiple COINs can be used with other Raman nanoparticles in order to provide multiplexing of signals.

In an embodiment, the Raman agent can be incorporated (e.g., disposed inside and/or attached to the surface of) or encapsulated into a biological agent (e.g., a cell or a virus). In particular, the Raman agent can be incorporated into stem cells, t-cells, bacterial strains, Red blood cells, white blood cells, and the like. As the encapsulating virus, bacteria, or stem cell moves through the body or within an area, the Raman imaging system can be used to monitor/track the virus, bacteria, or cell. Studying cell motility and tracking its natural distribution in the body is an important biological process that can offer scientists important information on how to better design diagnostics and therapeutics. By using a stem cell, for instance, incorporating a Raman agent (e.g. Raman active dyes or Raman nanoparticles) one could use the Raman signal to monitor its localization within the body after it has been administered for therapy for instance. One could also study the homing effects that bacteria, viruses, t-cells, or even macrophages have on tumor sites if these cells were to be previously encapsulated with Raman agents (e.g. Raman dyes or Raman nanoparticles). One could essentially use their Raman active signal as a reporter to track where exactly these cellular entities have localized after administration.

In an embodiment, the Raman compounds can include a reporter compound as noted above conjugated to a targeting ligand, so that the Raman agent or compound can have an affinity for a targeting ligand.

In an embodiment, the Raman agent can include a targeting ligand that is a chemical or biological ligand or compound having an affinity for one or more targets (e.g., also referred to as a "specific target" or "targeted area"). In an embodiment, the targeting ligand can include, but is not limited to, a drug, a therapeutic agent, a radiological agent, a chemological agent, a small molecule drug, a biological agent (e.g., antibodies, peptides, proteins, aptamers, antigens, and the like) and combinations thereof, that has an affinity for a target or a related biological event corresponding to the target (e.g., biomarkers). It should be noted that Raman agent modified with conjugation to other molecules (e.g., antibodies, proteins, peptides, aptamers, small molecules, and the like) in order to target the Raman agent to a particular molecular target are intended to be covered by embodiments of the present disclosure. For example, a Raman agent can be modified with a peptide so that it can target new blood vessels in tumors or a chemical associated with a specific cancer, tumor, or precancerous tissue. In an embodiment, the targeting ligand can have an affinity for a target such as cancer, tumor, precancerous cells or tissue, atherosclerosis, fibrosis. In another embodiment, the targeting ligand can be used for trafficking (where the Raman agent is incorporated into viruses or cells (e.g., stem cells, t-cells, Red blood cells, white blood cells, and the like)) to look at distribution in the body.

In an embodiment, the device does not necessarily need to use a "Raman agent", but can also utilize the intrinsic (or natural) Raman signal of the tissue itself or it can use contrast agents (such as fluorophores).

In an embodiment, the fluorescent agent can include fluorescent particle or dyes. In an embodiment, the fluorescent agent can include, but are not limited to, indocyanine green, methylene blue, and fluorescein or FITC.

In an embodiment, Raman agent and/or the fluorescent agent can be conjugated with one or more targeting agents (e.g., disease targeting compounds or ligands). The Raman agent and/or the fluorescent agent can then sensitively and specifically bind to the cells, proteins, and the like, related to the disease or condition of interest and their localization can be detected using the Raman probe.

It should be noted that the amount effective to result in uptake of the agent (e.g., fluorescent agent and/or Raman agent) into the cells or tissue of the subject depends upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

EXAMPLES

Now having described the embodiments of the present disclosure, in general, the example describes some additional embodiments of the present disclosure. While embodiments of the present disclosure are described in connection with the example and the corresponding text and figures, there is no intent to limit embodiments of the present disclosure to these descriptions. On the contrary, the intent is to cover all alternatives, modifications, and equivalents included within the spirit and scope of embodiments of the present disclosure.

Example 1

Design, Fabrication and Characterization of a Handheld Raman Device for Sensitively Detecting Tumor Targeted SERS Nanoparticles in Breast Cancer.

In order to help guide surgeons in the operating room in real-time, embodiments of the present disclosure provide for a handheld fiber-based Raman device specially designed for use in the clinic. Embodiments of the present disclosure have considered various parameters such as size, working distance, and acquisition timing in designing a handheld tool useful and compatible with existing surgical tools in the clinic.

An embodiment of the Raman probe includes a proximity sensor and a fluorescence wide field imaging component, where the fluorescence wide field imaging component offers the ability for wide field fluorescence imaging to help guide our Raman detection system and the proximity sensor can position the Raman probe the desired distance from the tissue.

Figure 1A:
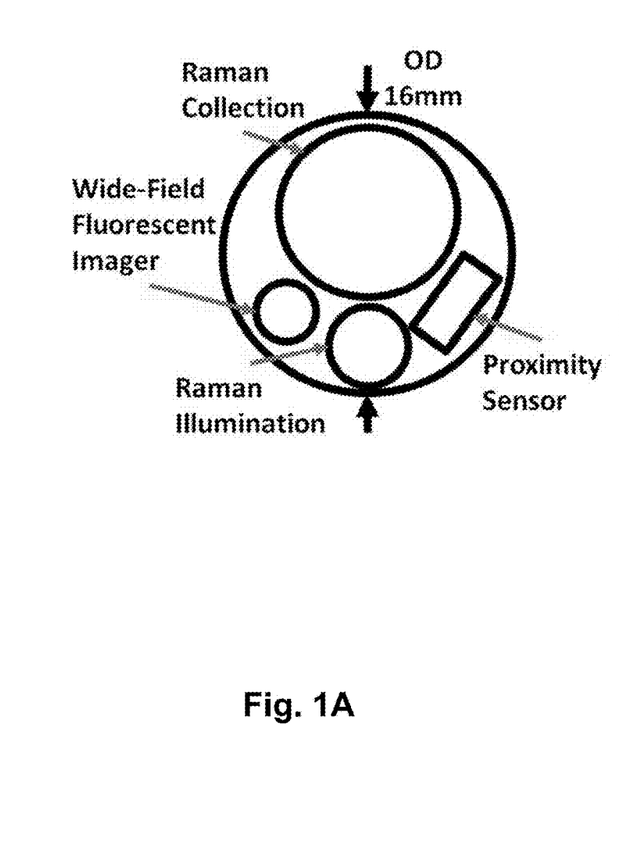
FIGS. 1A-B are example embodiments of the wide-field fluorescent image guided Raman spectrometer of the present disclosure.
Figure 1B:
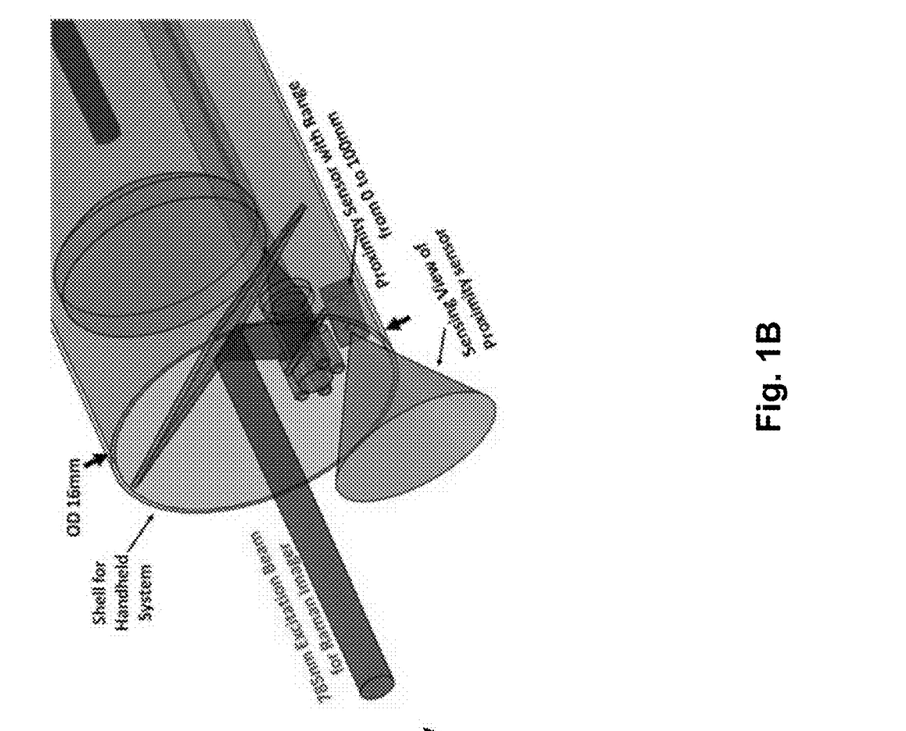

In an embodiment that can be used in an intraoperative setting. This allowed widening of the scope in order to accommodate for a lens of approximately 12 mm in diameter that would increase the Raman collection efficiency to about 9 times. As mentioned above, the Raman probe incorporates a feature that allows the device to correct for varying distances away from the tissue. Since there is a $1/r^2$ drop off with working distance away from the sample, a time of flight sensor (ST FlightSense™ technology) was incorporated (FIGS. 1A-B). The sensor is used to measure the distance away from the tissue and renormalize the signal due to the quadratic response seen with varying working distances, which allows determining differences in spectral Raman intensity in real time.

Figure 2A:
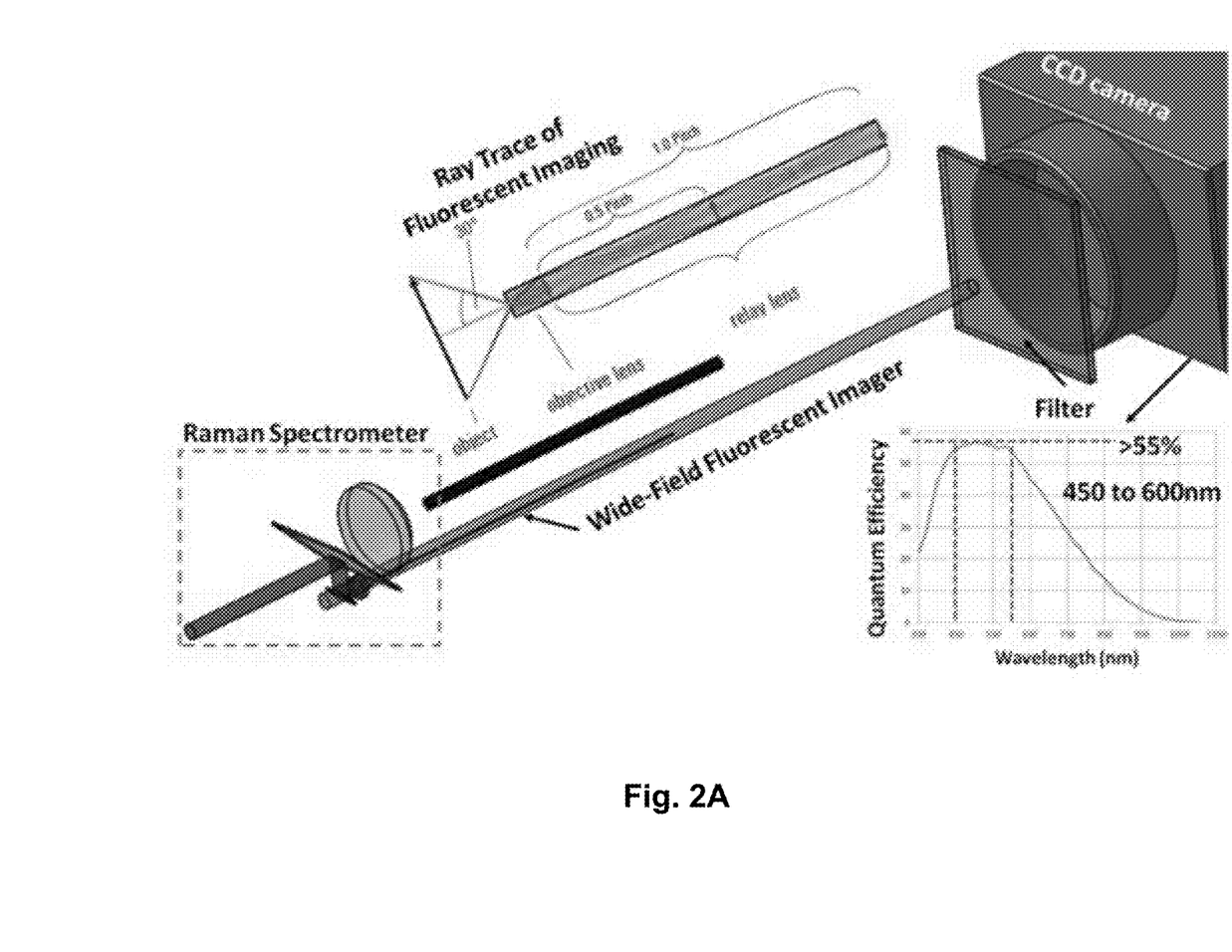
Figure 2B:
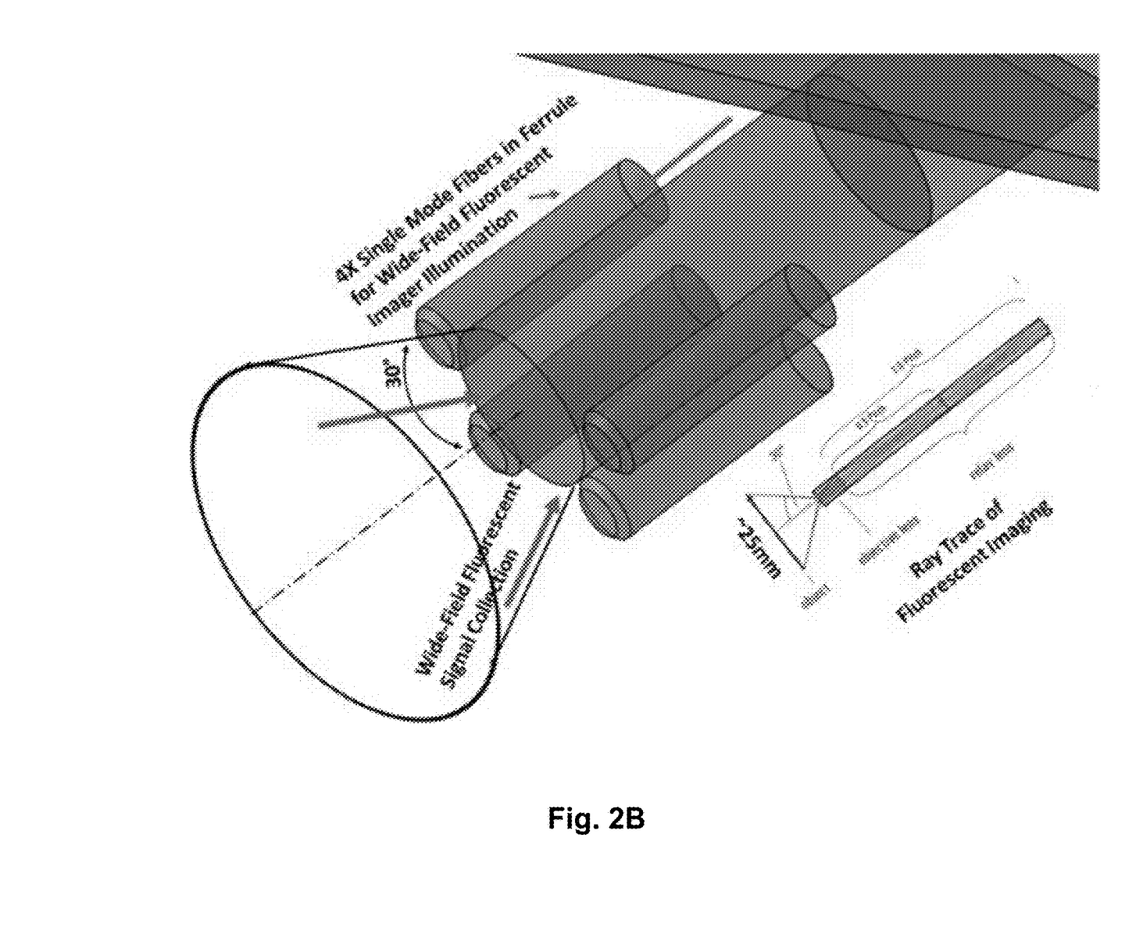
FIG. 2B demonstrates an example of how the wide-field fluorescent image can be acquired through a custom-made gradient-index (GRIN) optical lens with large field of view (half angle is around 30°, around 25 mm lateral field of view at the focus plane around 20 mm from the objective lens), which includes an objective lens and a relay lens. The ray trace of the fluorescent imaging is simulated in ZEMAX.

The wide field fluorescence component has also been integrated into the handheld design, creating a multimodal option during clinical use. The fluorescence image can be acquired using a custom made gradient index (GRIN) optical lens. Ray tracing was simulated using ZEMAX software to reveal a large 25 mm lateral field of view at the focal plane of about 20 mm from the objective lens (FIGS. 2A-B). This large field of view is meant to guide the surgeon in real time to the area of interest, then the surgeon can switch to the Raman point detection scheme in order to acquire multiplexed molecular information about the tumor margins.

Figure 3:
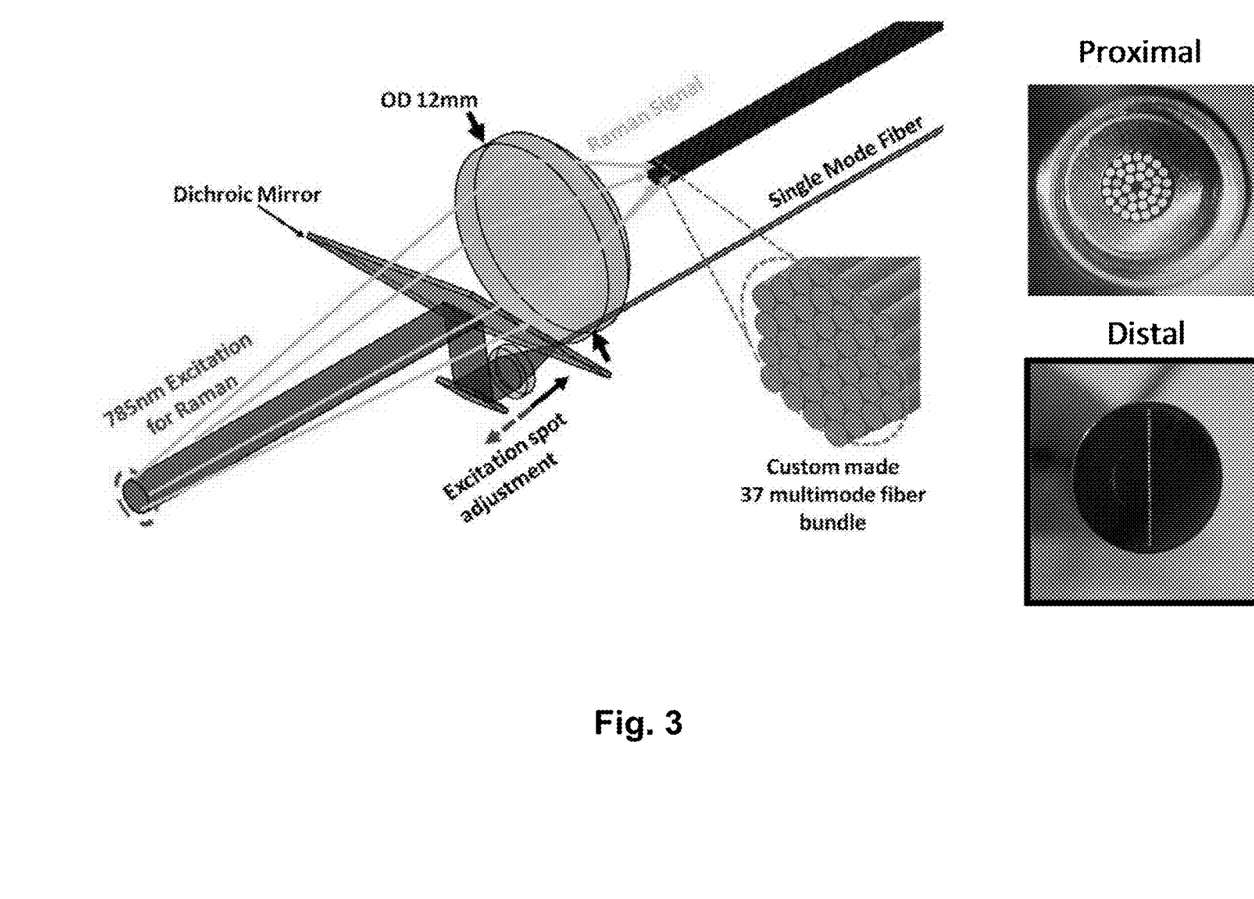
FIG. 3 is an example embodiment of the Raman spectrometer module, which includes a custom-made lenses for excitation and collection with OD of 3 mm and 12 mm respectively.

The Raman spectroscopy component has been designed to include a 37 multimode fiber bundle for collection and a single mode fiber which is slightly offset for excitation delivery of a 785 nm laser (FIG. 3). This setup can include a bandpass filter at the proximal end of the collection fiber rather than the distal end near the spectrometer. The fibers were then arranged in a linear array at the distal end to align perfectly within the slit of the spectrometer. There are interesting cell surface targets for breast cancer in addition to the ones we have already proposed to interrogate other types of tumors (e.g. head and neck cancers, melanoma, and pancreatic cancer). Some of the new breast cancer biomarkers that have been recently reported on include CD71, CD74, and CLDN1. A chemical conjugation scheme has been determined that works well with the described SERS nanoparticles and includes a bifunctional PEG linker that allows for amine chemistry with a specific antibody. The SERS nanoparticles can also be chemically conjugated to a fluorescent dye Alexa 640 for the dual modal imaging capabilities.

The Raman probe includes components that allow for: 1) dual modal fluorescence/Raman detection, 2) nine times more collection efficiency due to the larger diameter lens implemented, 3) time of flight proximity sensing to normalize the Raman signal for the quadratic drop off with working distance from sample surface.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding based on numerical value and the measurement techniques. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

At least the following is claimed:

1. A Raman probe comprising:
   a Raman detection system, wherein the Raman detection system is configured to illuminate an area of a subject or a sample with a light source and to receive Raman scattered light energy from the area;
   a time-of-flight proximity sensor system configured to measure the distance from the Raman probe to the area;
   a fluorescent imaging system configured to detect fluorescence from the area;
   an optical fiber system to direct light derived from the light source to the area and to further direct the Raman scattered light energy to the Raman detection system; and
   an optic system between the optical fiber system and the sample to concentrate the light onto the sample and to further collect the Raman scattered light energy from the sample, wherein the optic system further concentrates the collected Raman scattered light energy into the optical fiber system;
   wherein the optical fiber system includes a single fiber to guide light derived from the light source to the area, and
   wherein the optical fiber system includes a fiber bundle to guide Raman scattered light energy from the area to a Raman detection system.

2. The Raman probe of claim 1, wherein the light source is generated using one or more from the following group: a light emitting diode (LED), a laser, a diode laser, and a super luminescent laser diode (SLD).

3. The Raman probe of claim 1, wherein the Raman detector comprises at least one spectrometer.

4. The Raman probe of claim 1, further comprising an ultrasound transducer array.

5. A method of imaging, comprising:
   a) introducing a Raman probe of claim 1 to a subject;
   b) detecting fluorescent light from a first area of the subject;
   c) guiding the Raman probe to the first area based on the detected fluorescent light;
   d) positioning the Raman probe at a target distance from the first area, wherein the positioning at the target distance is determined using the proximity sensor system;
   e) exposing the first area to a light beam from the Raman detection system, wherein the light beam is scattered by a Raman agent associated with the first area, wherein the light beam that is scattered is referred to as a Raman scattered light energy;
   f) detecting the Raman scattered light using the Raman imaging device;
   q) repeating steps b) to f) for a plurality of areas, where each of the plurality of areas are different areas of the subject;
   h) acquiring the Raman scattered light energy from the first area and each of the plurality of areas; and
   i) forming a topological map of the area from the acquired Raman scattered light energy from the first area and each of the plurality of areas.

* * * * *